(12) United States Patent
Wang et al.

(10) Patent No.: US 11,486,798 B2
(45) Date of Patent: Nov. 1, 2022

(54) WATER QUALITY ANALYZER AND METHOD FOR ANALYZING WATER QUALITY

(71) Applicant: FUJIAN KELUNGDE ENV. TECH. CO., LTD, Fujian (CN)

(72) Inventors: Shuiji Wang, Fujian (CN); Jianping Cui, Fujian (CN)

(73) Assignee: FUJIAN KELUNGDE ENV. TECH. CO., LTD, Zhangzhou (CN)

( * ) Notice: Subject to any disclaimer, the term of this patent is extended or adjusted under 35 U.S.C. 154(b) by 630 days.

(21) Appl. No.: 16/574,345

(22) Filed: Sep. 18, 2019

(65) Prior Publication Data

US 2020/0011770 A1     Jan. 9, 2020

Related U.S. Application Data

(63) Continuation of application No. PCT/CN2018/078821, filed on Mar. 13, 2018.

(30) Foreign Application Priority Data

Jun. 21, 2017   (CN) .......................... 201710474827.X

(51) Int. Cl.
*G01N 1/14*      (2006.01)
*G01N 33/18*     (2006.01)
*G01J 3/02*      (2006.01)
*G01N 35/08*     (2006.01)

(52) U.S. Cl.
CPC ........... *G01N 1/14* (2013.01); *G01N 33/1853* (2013.01); *G01J 3/0251* (2013.01); *G01N 35/085* (2013.01)

(58) Field of Classification Search
CPC ............................. G01N 1/14; G01N 33/1853
See application file for complete search history.

(56) References Cited

U.S. PATENT DOCUMENTS

| 3,728,080 A | * | 4/1973 | Moran | G01N 35/021 |
| | | | | 702/108 |
| 4,523,484 A | * | 6/1985 | Kadota | G01N 1/38 |
| | | | | 73/864.22 |
| 2007/0104614 A1 | * | 5/2007 | Wang | G01N 35/00594 |
| | | | | 422/64 |

FOREIGN PATENT DOCUMENTS

| CN | 1963527 A | 5/2007 |
| CN | 201096655 Y | 8/2008 |

(Continued)

*Primary Examiner* — Brian R Gordon
*Assistant Examiner* — Dwan A Gerido

(57) ABSTRACT

Disclosed are a water quality analyzer and a method for analyzing water quality. The water quality analyzer includes a first disc system, a second disc system, a colorimetric system, a cleaning system, a mechanical sampling system, an analysis system and a central control display. The first disc system and the second disc system are axially rotatable. A plurality of sample locating positions and a chemical locating positions are provided on the first disc system along a circumference of the first disc system. A plurality of colorimetric cuvette locating positions are provided on the second disc system, and the colorimetric system is arranged at a circumference edge of the second disc system. The cleaning system and the mechanical sampling system are provided between the first disc system and the second disc system. The method includes water sampling, water sample injection, cleaning, reagent extraction, reagent injection, cleaning and colorimetric analysis.

6 Claims, 5 Drawing Sheets

(56) References Cited

FOREIGN PATENT DOCUMENTS

| CN | 203720190 U | 7/2014 |
| CN | 104502618 A | 4/2015 |

\* cited by examiner

WATER QUALITY ANALYZER AND METHOD FOR ANALYZING WATER QUALITY

CROSS-REFERENCE TO RELATED APPLICATIONS

This application is a continuation of International Patent Application No. PCT/CN2018/078821, filed on Mar. 13, 2018, which claims the benefit of priority from Chinese Application No. 201710474827.X, filed on Jun. 21, 2017. The entire contents of the aforementioned applications, including any intervening amendments thereto, are incorporated herein by reference.

TECHNICAL FIELD

The present application relates to water quality analysis, more particularly, to a water quality analyzer and a method for analyzing water quality.

BACKGROUND OF THE INVENTION

A water quality analyzer, based on the water analysis method (e.g. flow injection analysis, LFA analysis, sequential injection analysis, colorimetry, etc.), is often used to analyze the water quality of tap water, surface water, wastewater, ocean water, etc. The colorimetry is a highly accurate quantitative analysis method having a highly sensitive and highly selective reaction and a constant and relatively stable colored reaction product, which determines the content of a component by comparing or measuring the intensity of the color of a colored solution. Photoelectric colorimetry is to draw a standard curve according to the measurement of the absorbance of a series of standard solutions with a photoelectric colorimeter, and then determine the content of a solution by calculating the absorbance thereof using the standard curve.

SUMMARY OF THE INVENTION

The water quality analyzer in the prior art has the following deficiencies.
1. The existing water quality analyzers cannot perform in situ measurement, because only four water quality parameters can be measured at a time, causing a low-speed analysis. However, multiple water quality parameters are required to be analyzed, and thus, each analysis cannot take a long time.
2. Generally, the sampling needle can only be used for sampling, and samples are mixed by a mixing device. Therefore, the existing water quality analyzers have complicated structures and high costs.

In view of this, the present invention provides a water quality analyzer and a method for analyzing water quality to analyze multiple water quality parameters at a time, realizing a highly effective analysis for water quality analysis.

A water quality analyzer, comprising a first disc system, a second disc system, a colorimetric system, a cleaning system, a mechanical sampling system, an analysis system and a central control display; where the first disc system and the second disc system are axially rotatable; a plurality of sample locating positions and reagent locating positions are provided on the first disc system along a circumference of the first disc system; a plurality of colorimetric cuvettes locating positions are provided on the second disc system, and the colorimetric system is arranged on the circumference edge of the second disc system; the cleaning system and the mechanical sampling system are provided between the first disc system and the second disc system; the analysis system is connected to the colorimetric system to analyze a water quality parameter and send the water quality parameter to the central control display; and the mechanical sampling system comprises an height control motor, a rotation control motor, a sampling arm, a sampling needle, a control board, a mixing tube and a plunger pump; the height control motor and the rotation control motor are mounted below the sampling arm, and are configured to control up-down movement and rotation of the sampling arm respectively; the sampling needle is mounted at an end of the sampling arm and connected to the control board; and one end of the mixing tube is connected with the sampling needle and the other end of the mixing tube is connected to the plunger pump.

In some embodiments, the water quality analyzer further comprises an in situ sampling position which is disposed on a side of the mechanical sampling system and comprises a peristaltic pump, a delivery tube, and an in situ sampling position which are sequentially connected.

In some embodiments, the sampling arm comprises a rotating shaft and a panel connected to an end of the rotating shaft; and the rotating shaft is provided with a through hole through which a pipe and a wire pass.

In some embodiments, the control board is provided with a sampling needle level sensor.

In some embodiments, the cleaning system comprises a cleaning tank and a cleaning pump, a cleaning liquid container and a waste container; the cleaning tank is provided between the first disc system and the second disc system; a hollow cleaning column is provided at the cleaning tank; a waste outlet is provided on a bottom of the cleaning tank; the cleaning pump is connected with the mixing tube of the mechanical sampling system and the cleaning liquid container respectively; and the waste container is connected to the waste outlet.

In some embodiments, liquid level sensors are respectively provided on a bottom of the cleaning liquid container and an upper portion of the waste container; and the liquid level sensors are connected to the central control display.

In some embodiments, the water quality analyzer further comprises a cleaning workstation which is arranged on a side of the colorimetric system.

A method for analyzing water quality using the water quality analyzer provided by the present invention comprises:
S1) rotating the sampling arm to the in situ sampling position or the sample locating position, extracting a water sample, by the plunger pump, from the in situ sampling position or the sample locating position into the mixing tube via the sampling needle;
S2) rotating the sampling arm to the colorimetric cuvette locating position, and with control of the plunger pump, injecting the water sample from the mixing tube to a plurality of colorimetric cuvettes via the sampling needle;
S3) rotating the sampling arm to the cleaning system to clean the sampling needle and the mixing tube;
S4) rotating the sampling arm to a reagent locating position, and with control of the plunger pump, extracting a reagent from a test tube on the reagent locating position into the mixing tube via the sampling needle;
S5) rotating the sampling arm to the colorimetric cuvette locating position; with control of the plunger pump, injecting the reagent from the mixing tube into the colorimetric cuvettes containing the water sample via the sampling needle; and mixing the reagent with the water sample by the sampling arm;

S6) rotating the sampling arm to the cleaning system to clean the sampling needle and the mixing tube;

S7) rotating the second disc system to allow the plurality of the colorimetric cuvettes to sequentially pass through the colorimetric system to determine a water quality data; sending the water quality parameter to the analysis system; and sending the water quality parameter to the central control display.

In some embodiments, the method further comprises step 8 comprising rotating the colorimetric cuvettes to the cleaning workstation to clean the colorimetric cuvettes.

In some embodiments, the step of cleaning the sampling needle and the mixing tube in step 3 or step 6 comprises:

rotating the sampling arm above the cleaning tank, and extracting a cleaning liquid from the cleaning liquid container by the plunger pump to clean the mixing tube, then rotating the sampling arm and lowering the sampling needle into the cleaning column;

starting the cleaning pump to extract the cleaning liquid from the cleaning liquid container, through the mixing tube to the sampling needle, and finally to the cleaning column;

cleaning an exterior of the sampling needle as the cleaning liquid overflows; and sensing, by the control board, a level of the cleaning liquid and sending out a signal to turn off the cleaning pump; and draining the cleaning liquid into the waste container via the waste outlet on the bottom of the cleaning tank.

The liquid level sensor mounted on the bottom of cleaning liquid container is configured to sense a signal of exhaustion of the cleaning liquid; and the liquid level sensor mounted on the upper portion of the waste container is configured to sense a signal of overflow of the cleaning liquid; and the signals are sent to the central control display.

In some embodiments, in step 5, the step of mixing comprises: repeating one or both of the following:

a) mixing the reagent with the water sample by releasing external air into a colorimetric cuvette as the mixing tube is inserted into the colorimetric cuvette, wherein the external air is pumped into the mixing tube by the plunger pump; and b) mixing the reagent with the water sample by injecting a mixture of the chemical and the water sample from the sampling needle into a colorimetric cuvette as the sampling arm is lifted, wherein the mixture of the chemical and the water is extracted from the colorimetric cuvette into the mixing tube by the plunger pump.

The present application has the following benefits.

1. The present application is able to analyze multiple water quality parameters in a fast speed, and initial absorbance (abs-s) of the water quality can be read through the colorimetric system, and the analysis parameters can be adjusted based on requirements.

2. The mixing tube and the plunger pump are arranged at the sampling needle, such that the sampling and mixing are performed at the same time, which means the size and the cost of the water quality analyzer can be effectively reduced.

3. The water sample can be extracted in situ into the in situ sampling position by the peristaltic pump of the in situ sampling position to perform an in situ water sample analysis.

4. The water quality analyzer of the present invention is highly automated since the mixing tube and the sampling needle can be cleaned by the cleaning system and the colorimetric cuvette can be cleaned by the cleaning workstation.

Figure 1:
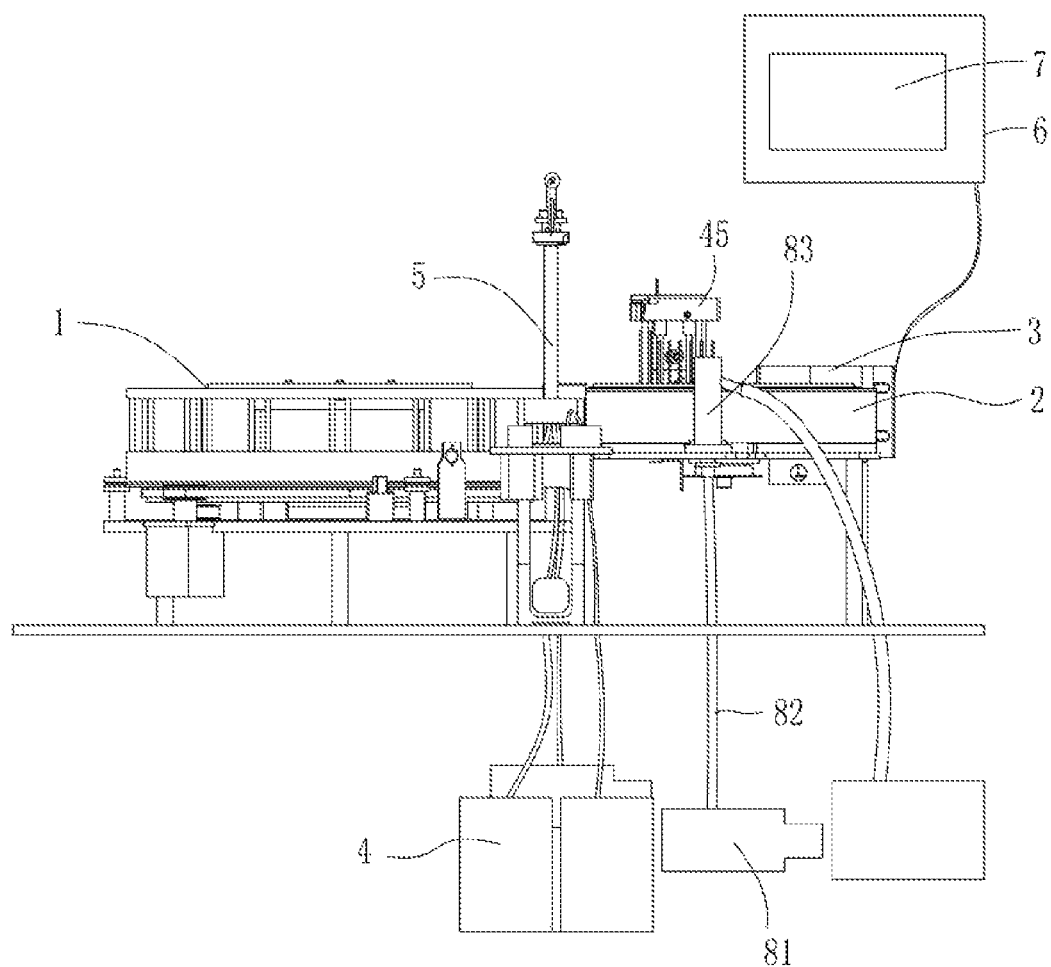
FIG. 1 is a front view of a water quality analyzer according to the present invention.

REFERENCE NUMERALS 1, first disc system;
11, sample locating position;
12, reagent locating position;
2, second disc system;
21, colorimetric cuvette locating system;
3, colorimetric system;
4, cleaning system;
41, cleaning tank;
411, cleaning column;
412, waste outlet;
42, cleaning pump;
43, cleaning liquid container;
44, waste container;
45, cleaning workstation;
5, mechanical sampling system;
51, height control motor;
52, rotation control motor;
53, sampling arm;
531, rotating shaft;
532, panel;
533, through hole;
54, sampling needle;
55, control board;
551, sampling needle level sensor;
56, mixing tube;
57, plunger pump;
6, analysis system;
7, central control display;
8, in situ water sampling system;
81, peristaltic pump;
82, delivery tube;
83, in-situ sampling position;
9, level sensor.

DETAILED DESCRIPTION OF EMBODIMENTS

The present invention will be further described in detail below with reference to the accompanying drawings and embodiments to make the objects, technical solutions and advantages of the present invention more comprehensible.

As shown in FIG. 1, illustrated is a water quality analyzer, comprising a first disc system 1, a second disc system 2, a colorimetric system 3, a cleaning system 4, a mechanical sampling system 5, an analysis system 6, a central control display 7 and an in situ water sampling system 8.

Figure 2:
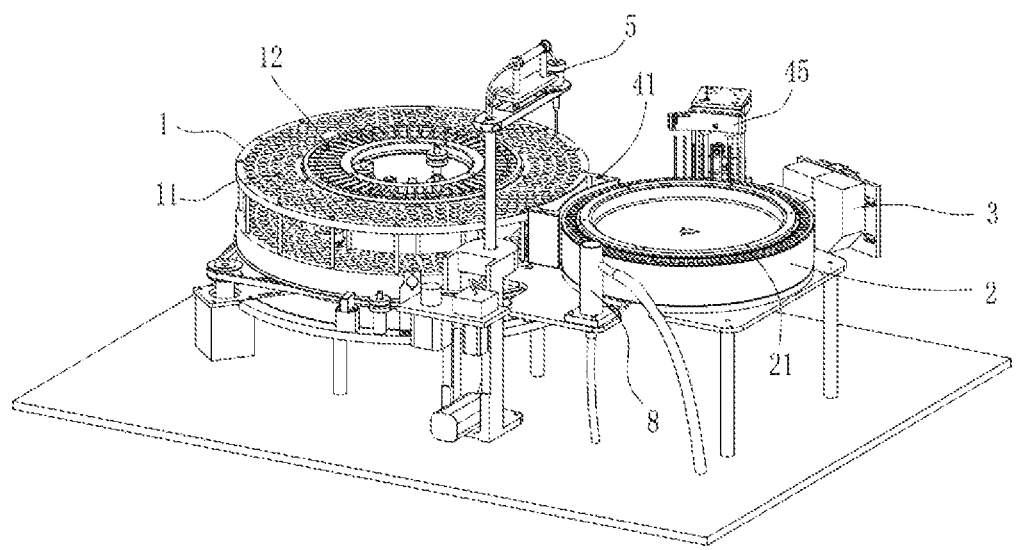
FIG. 2 is a perspective view of the water quality analyzer, in which a lower portion is not shown.
Figure 3:
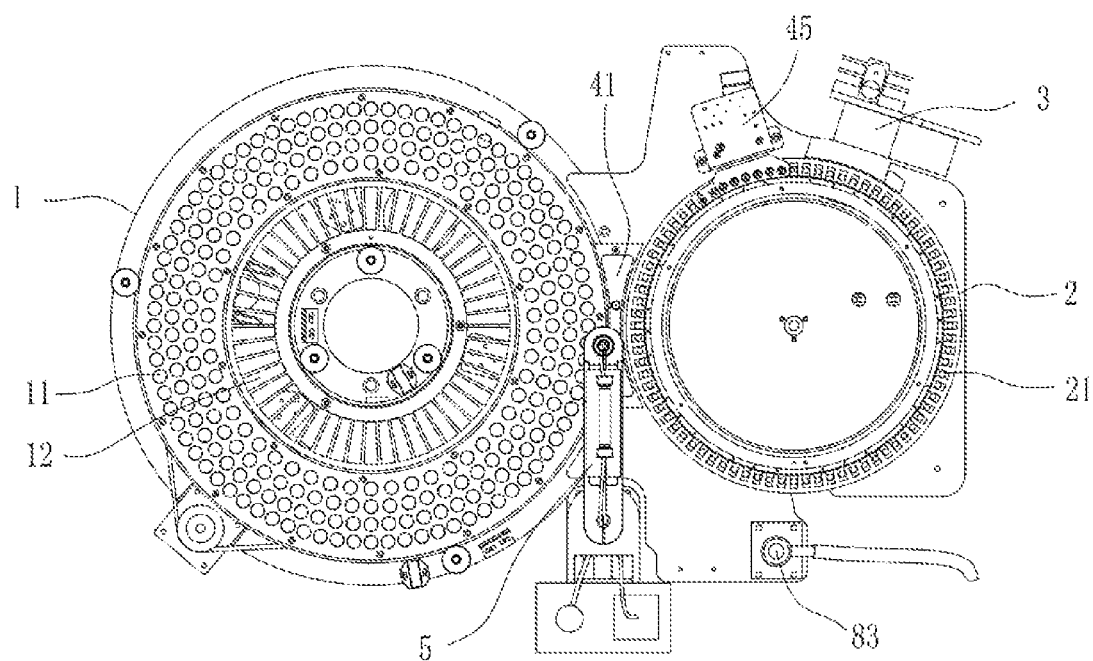
FIG. 3 is a top view of FIG. 1.

As shown in FIGS. 2-3, the first disc system 1 is provided with a rotary motor which is axially arranged, such that the first disc system 1 may rotate axially. A plurality of sample locating positions 11 and a plurality of reagent locating positions 12 are provided on the first disc system along a circumference of the first disc system, and the sample locating position 11 is disposed on the outer circumference of the reagent locating position 12. The second disc system 2 is provided with a rotary motor which is axially arranged, such that the second disc system 2 may rotate axially. A plurality of colorimetric cuvettes locating positions 21 are provided on the second disc system 1.

The analysis system 6 is arranged at a circumferential edge of the second disc system 2, and is connected to the colorimetric system 3 for analyzing water quality parameters and further transmitting the water quality parameters to the central control display 7.

Figure 4:
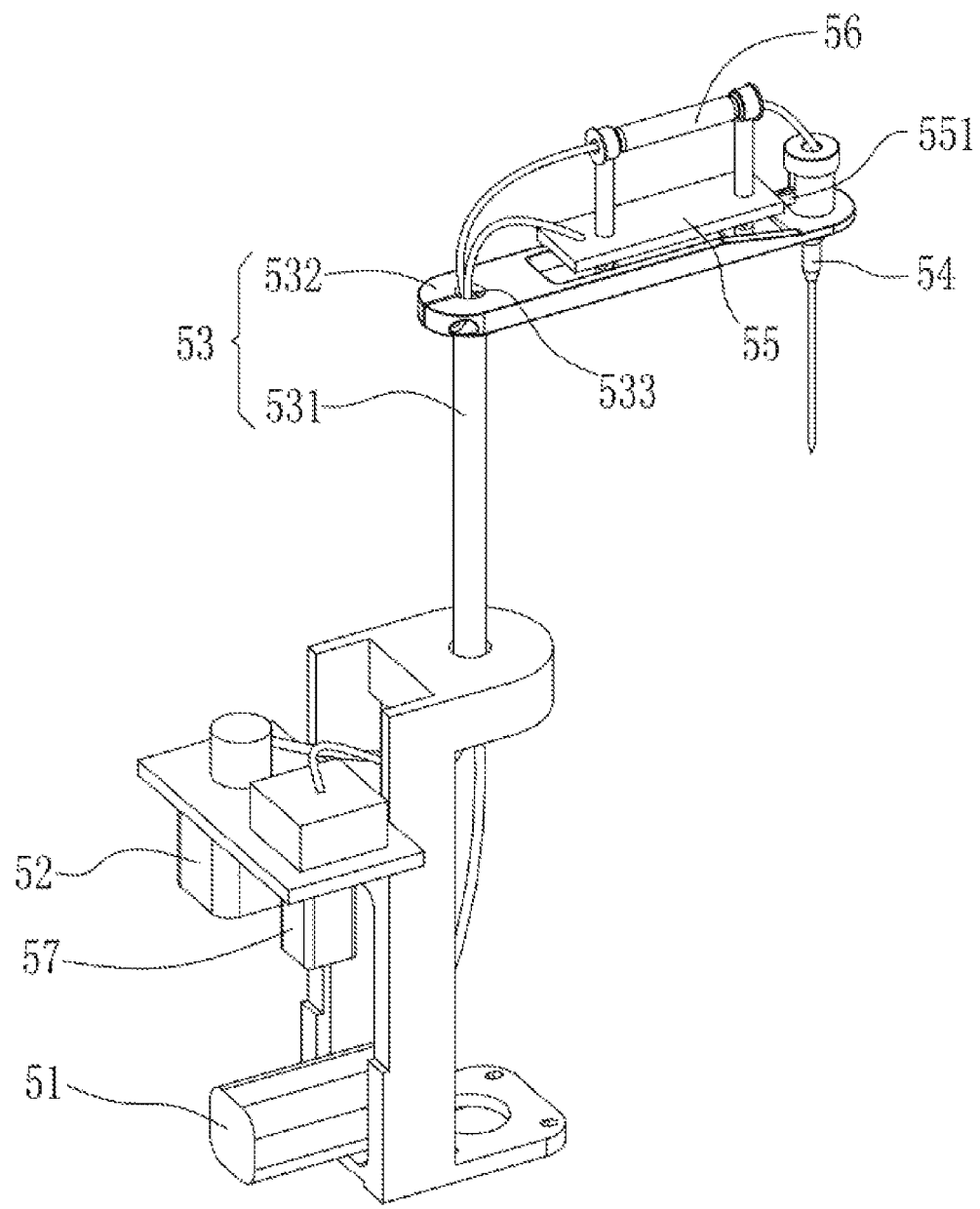
FIG. 4 is a schematic diagram of a mechanical sampling system of the water quality analyzer.

As shown in FIG. 4, a mechanical sampling system 5 is provided between the first disc system 1 and the second disc system 2 and comprises an height control motor 51, a rotation control motor 52, a sampling arm 53, a sampling needle 54, a control board 55, a mixing tube 56, and a plunger pump 57. The height control motor 51 and the rotation control motor 52 are mounted below the sampling arm 53, and are configured to control up-down movement and rotation of the sampling arm 53 respectively. The sampling needle 54 is mounted at an end of the sampling arm 53 and connected to the control board 55 which is mounted with a sampling needle level sensor 551. One end of the mixing tube 56 is connected with the sampling needle 54 and the other end of the mixing tube is connected to the plunger pump 57. The sampling arm comprises a rotating shaft 531 and a panel 532 connected to an end of the rotating shaft 531; and the rotating shaft is provided with a through hole 533 through which a pipe and a wire pass.

Figure 5:
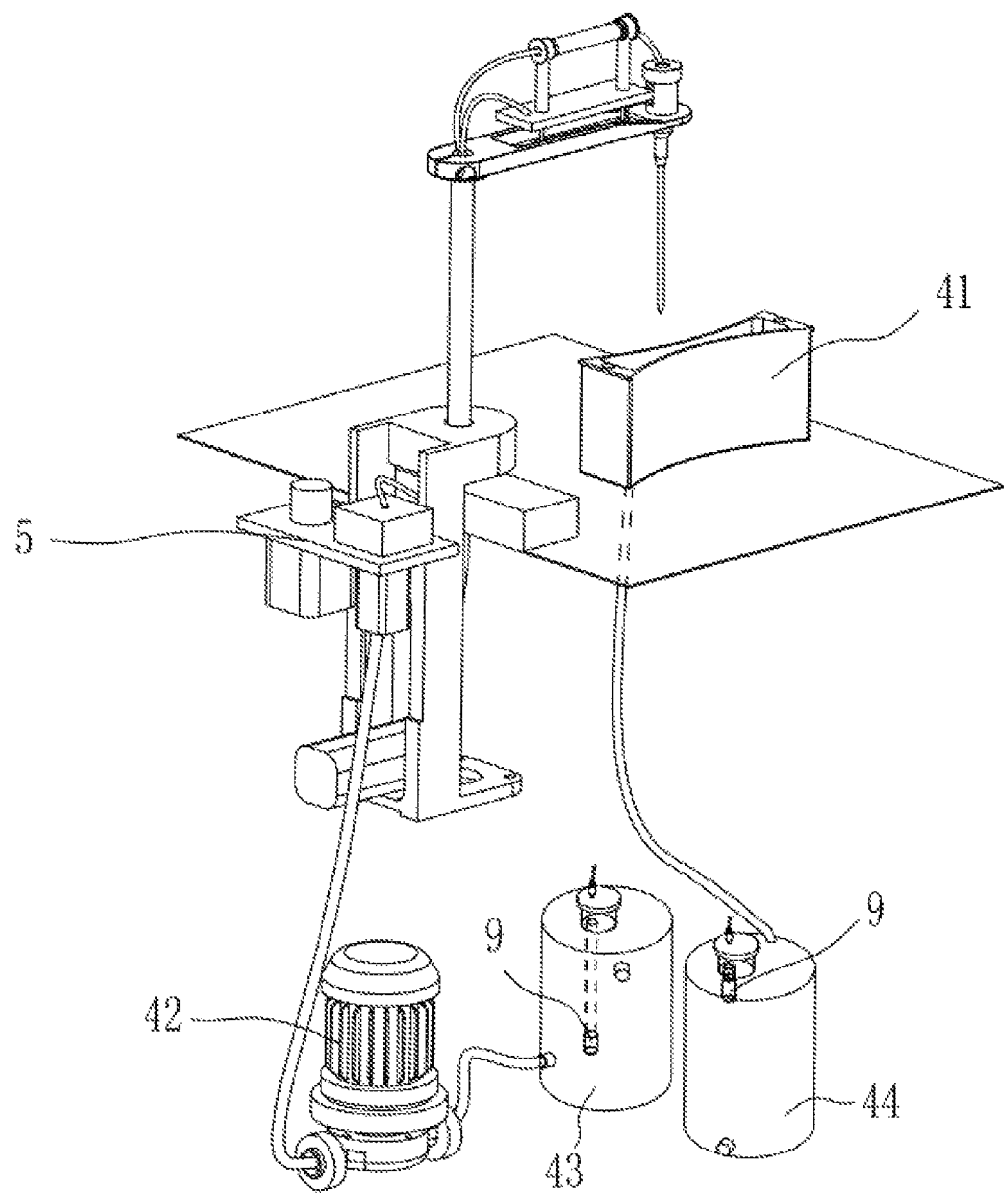
FIG. 5 is a schematic diagram of a cleaning sampling system of the water quality analyzer.
Figure 6:
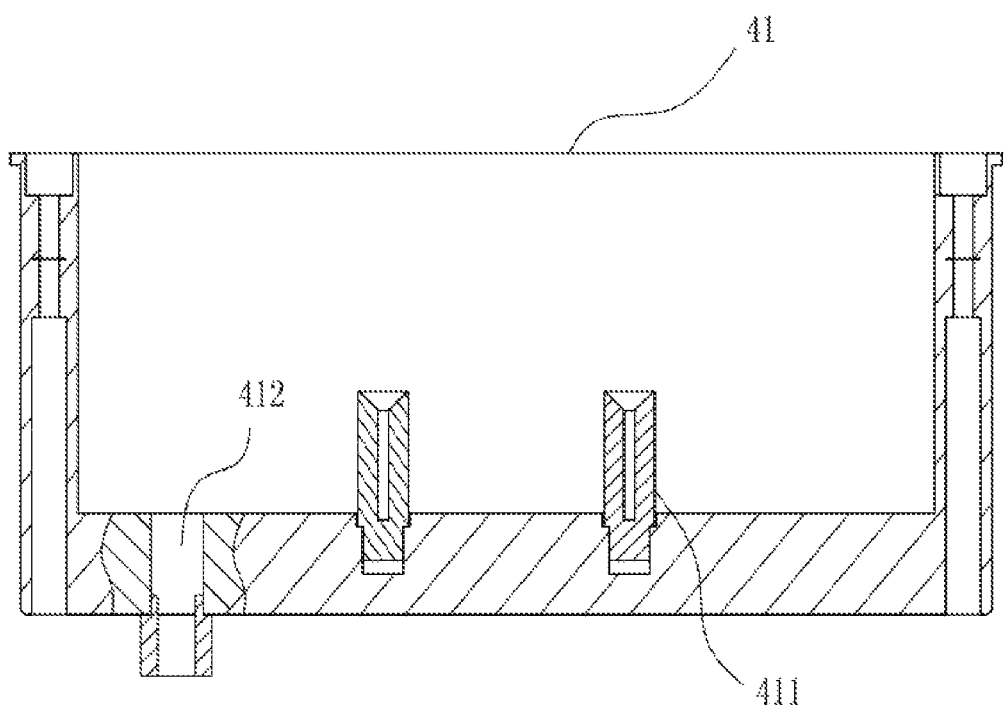
FIG. 6 is a sectional view of a cleaning tank of the water quality analyzer.

As shown in FIGS. 5-6, the cleaning system 4 is provided between the first disc system 1 and the second disc system 2 and comprises a cleaning tank 41 and a cleaning pump 42, a cleaning liquid container 43, and a waste container 44. The cleaning tank 41 is provided between the first disc system 1 and the second disc system 2; a hollow cleaning column 411 is provided at the cleaning tank 41; a waste outlet 412 is provided on a bottom of the cleaning tank 41. The cleaning pump 42 is connected with the mixing tube 56 of the mechanical sampling system 5 and the cleaning liquid container 43 respectively; and the waste container 44 is connected to the waste outlet 412. Liquid level sensors 9 are respectively provided on a bottom of the cleaning liquid container 43 and an upper portion of the waste container 44, and the liquid level sensors are connected with the central control display 7.

The in situ water sampling system 8 is provided on the side of the mechanical sampling system 5 and comprises a peristaltic pump 81, a delivery tube 82, and an in situ sampling position 83 which are sequentially connected.

The cleaning workstation 45 is arranged on the side of the colorimetric system 3 to clean the colorimetric cuvettes.

A method for analyzing water quality using the water quality analyzer is further provided by the present invention and comprises the following steps.

S1) Water Sampling

As the sampling arm 53 rotated to the in situ sampling position 83 or the sample locating position 11, the water sample from the sample locating position 11 or the in situ sampling position 83 is extracted into the mixing tube 56 by the plunger pump via the sampling needle 54. Specifically, an end of the sampling needle 54 is lowered into the water sample and stopped when the sampling needle level sensor 551 sensed a liquid level, and then the extraction of the water sample begins.

The water sample can be extracted in situ via the in situ sample position 83. The peristaltic pump 81 is turned on when pipes of the peristaltic pump contacts with the water source, so water is extracted into the in situ sampling position 83 via delivery tube, and then a precise amount of water from the in situ sampling position 83 is extracted into the mixing tube 56 by the plunger pump 57 via sampling arm 53.

The water source sampled into the laboratory can be put into a test tube and placed on the sample locating position 11, and the sampling arm 53 is rotated above the sample locating position, and then the sampling needle 54 is inserted into the test tube and extracts the water sample into the mixing tube 56.

S2) Water Sample Injection

The sampling arm 53 is rotated to a colorimetric cuvette locating position 21, and then with control of the plunger pump, the water sample from the mixing tube 56 is injected into a plurality of colorimetric cuvettes via the sampling needle 54.

Multiple parameters are required to analyze the water quality, and the water quality analyzer of the present invention is capable of analyzing more than eight parameters at a time, such that the water sample can be injected into more than eight cuvettes to facilitate the simultaneous analysis of multiple parameters in the subsequent process.

S3) Cleaning

The sampling arm 53 is rotated to the cleaning system 4 to clean the sampling needle 54 and the mixing tube 56, and specifically, the sampling arm 53 us rotated above the cleaning tank 41, and the mixing tube 56 is cleaned by the cleaning liquid which is extracted from the cleaning liquid container 43 by the cleaning pump 42. Then, the sampling arm 53 is rotated so that the sampling needle 54 is lowered and inserted into the cleaning column 411. The cleaning pump 42 is started to extract the cleaning liquid, from the cleaning liquid container 43, through the mixing tube 56 to the sampling needle 54, and finally to the cleaning column 411. An exterior of the sampling needle 54 is cleaned as the cleaning liquid overflows. When a level of the cleaning liquid is sensed, by the control board 55, a signal is sent out to turn off the cleaning pump 42; and the cleaning liquid is drained into the waste container via the waste outlet 412 on the bottom of the cleaning tank 41.

The liquid level sensors 9 mounted on the bottom of cleaning liquid container 43 is configured to sense a signal of exhaustion of the cleaning liquid; and the liquid level sensor mounted on the upper portion of the waste container is configured to sense a signal of overflow of the cleaning liquid; and the signals are sent to the central control display 7. When the cleaning liquid is used up, a warning will be shown on the central control display 7 to remind the operators to add the cleaning liquid. When the waste liquid is overflowed, a warning will be shown on the central control display 7 to remind the operators to empty the waste container.

S4) Reagent Extraction

As the sampling arm 53 is rotated to a reagent locating position 12, a reagent from the test tube on the reagent locating position 12 is extracted into the mixing tube 56 by the plunger pump 57 via the sampling needle 54. Specifically, an end of the sampling needle 52 is lowered into the reagent, and the sampling needle stops lowering when the sampling needle level sensor 551 sensed a liquid level of the reagent, and the extraction for the reagent begins.

S5) Reagent Injection

The sampling arm 53 is rotated to a colorimetric cuvette locating position 21, and with control of the plunger pump 57, the reagent from the mixing tube 56 is injected into the colorimetric cuvettes containing the water sample via the sampling needle 54. The reagent is injected to each colorimetric cuvette, and with the sampling arm 53, the water sample is mixed with the reagent by repeating one or both of following:

a) in order to mix the reagent with the water sample, the external air pumped into the mixing tube 56 by the plunger pump 57 is released when the mixing tube 56 is inserted into the colorimetric cuvette; and b) in order to mix the reagent with the water sample, a mixture of the reagent and the water sample in the colorimetric cuvette is extracted into the mixing tube 56 controlled by the plunger pump 57 and injected back to the colorimetric cuvette from the sampling needle 54 as the sampling arm 53 lifted up.

S6) Cleaning

The sampling arm 53 is rotated to the cleaning system 4 to clean the sampling needle 54 and the mixing tube 56, and the step of cleaning is as same as the cleaning in step 3.

S7) Colorimetric Analysis

When the colorimetric cuvettes sequentially passes the colorimetric system 3 as the second disc system 2 rotates, a water quality data is determined and is sent to the analysis system 6, and the water quality parameter is sent to the central control display 7.

The colorimetric system 6 is provided with a set of standard filter discs ranging from light to dark, divided into red, yellow and blue families. By rotating the filter disc, the color, hue and color value of the water quality are measured and analyzed, and the final absorbance (abs-e) of the water quality is read.

S8) The Cleaning for the Colorimetric Cuvette

The colorimetric cuvettes are rotated to the cleaning workstation 45 to clean the colorimetric cuvettes.

An in situ intermittent water quality analysis can be achieved by the present application which is capable of analyzing multiple parameters in a high speed. Therefore, the present application has a promising application prospect.

Any changes or modifications that can be easily conceived by the skilled in the art based on the present application shall fall within the scope of the present invention.

INDUSTRIAL APPLICATION

The present application can be applied to analyze the water quality of tap water, surface water, wastewater, ocean water, etc., thus identifying the chemical components in water and determining contents thereof.

We claim:

1. A water quality analyzer, comprising a first disc system, a second disc system, a colorimetric system, a cleaning system, a mechanical sampling system, an analysis system and a central control display;

wherein the first disc system and the second disc system are axially rotatable; a plurality of sample locating positions and a plurality of reagent locating positions are provided on the first disc system along a circumference of the first disc system; a plurality of cuvette locating positions are provided on the second disc system, and the colorimetric system is arranged at a circumference edge of the second disc system; the cleaning system and the mechanical sampling system are provided between the first disc system and the second disc system; the analysis system is connected to the colorimetric system to analyze a water quality parameter and send the water quality parameter to the central control display;

the mechanical sampling system comprises a height control motor, a rotation control motor, a sampling arm, a sampling needle, a control board, a mixing tube and a plunger pump; the height control motor and the rotation control motor are mounted below the sampling arm, and are configured to control up-down movement and rotation of the sampling arm respectively; the sampling needle is mounted at an end of the sampling arm and connected to the control board; and one end of the mixing tube is connected with the sampling needle, and the other end of the mixing tube is connected to the plunger pump;

the cleaning system comprises a cleaning tank and a cleaning pump, a cleaning liquid container and a waste container; the cleaning tank is provided between the first disc system and the second disc system; a hollow cleaning column is provided at the cleaning tank; a waste outlet is provided on a bottom of the cleaning tank; the cleaning pump is connected with the mixing tube of the mechanical sampling system and the cleaning liquid container respectively; and the waste container is connected to the waste outlet; and liquid level sensors are respectively provided on a bottom of the cleaning liquid container and an upper portion of the waste container; and the liquid level sensors are connected to the central control display.

2. The water quality analyzer of claim 1, further comprising a cleaning workstation which is arranged on a side of the colorimetric system.

3. The water quality analyzer of claim 1, further comprising a cleaning workstation which is arranged on a side of the colorimetric system.

4. A method for analyzing water quality using the water quality analyzer of claim 1, comprising:

1) rotating the sampling arm to the in situ sampling position or the sample locating position; extracting a water sample, by the plunger pump, from the in situ sampling position or the sample locating position into the mixing tube via the sampling needle;

2) rotating the sampling arm to the cuvette locating positions; and with control of the plunger pump, injecting the water sample from the mixing tube to a plurality of cuvettes via the sampling needle;

3) rotating the sampling arm to the cleaning system to clean the sampling needle and the mixing tube;

4) rotating the sampling arm to a reagent locating position; and with control of the plunger pump, extracting a reagent from a test tube on the reagent locating position into the mixing tube via the sampling needle;

5) rotating the sampling arm to the cuvette locating positions; with control of the plunger pump, injecting the reagent from the mixing tube into the cuvettes containing the water sample via the sampling needle; and mixing the reagent with the water sample by the sampling arm;

6) rotating the sampling arm to the cleaning system to clean the sampling needle and the mixing tube; and 7) rotating the second disc system to allow the cuvettes to sequentially pass through the colorimetric system to determine a water quality data; sending the water quality data to the analysis system; and sending the water quality parameter to the central control display;

wherein the step of cleaning the sampling needle and the mixing tube in step 3) or step 6) comprises:

rotating the sampling arm above the cleaning tank, and extracting a cleaning liquid from the cleaning liquid container by the plunger pump to clean the mixing tube, and then rotating the sampling arm and lowering the sampling needle into the cleaning column;

starting the cleaning pump to extract the cleaning liquid from the cleaning liquid container, through the mixing tube to the sampling needle, and finally to the cleaning column;

cleaning an exterior of the sampling needle as the cleaning liquid overflows; and sensing, by the control board, a level of the cleaning liquid; and sending out a signal to turn off the cleaning pump; and draining the cleaning liquid into the waste container via the waste outlet on the bottom of the cleaning tank.

5. The method of claim 4, wherein the liquid level sensor mounted on the bottom of cleaning liquid container is configured to sense a signal of exhaustion of the cleaning liquid; and the liquid level sensor mounted on the upper portion of the waste container is configured to sense a signal of overflow of the cleaning liquid; and the signals are sent to the central control display.

6. The method of claim 4, wherein the mixing in step comprises: repeating one or both of the following:
   a) mixing the reagent with the water sample by releasing external air into a cuvette as the mixing tube is inserted into the cuvette, wherein the external air is pumped into the mixing tube by the plunger pump; and
   b) mixing the reagent with the water sample by injecting a mixture of the reagent and the water sample from the sampling needle into a cuvette as the sampling arm is lifted, wherein the mixture of the reagent and the water is extracted from the cuvette into the mixing tube by the plunger pump.

* * * * *